United States Patent [19]

Guillon et al.

[11] Patent Number: 4,601,901

[45] Date of Patent: * Jul. 22, 1986

[54] ANHYDROUS NAIL LACQUER CONTAINING AS A RESIN A COPOLYMER COMPRISING UNITS OF VINYLSULFONAMIDE OR A UNSATURATED AMIDE AND OF AN ALKYL ACRYLATE OR METHACRYLATE

[75] Inventors: Michel Guillon, Bourg-La-Reine; Jean Mondet, Sevran; Christos Papantoniou, Montmorency; Claudine Vandenbossche, Aulnay-Sous-Bois, all of France

[73] Assignee: Societe Anonyme dite: L'Oreal, Paris, France

[ * ] Notice: The portion of the term of this patent subsequent to Jun. 5, 2001 has been disclaimed.

[21] Appl. No.: 528,810

[22] Filed: Sep. 2, 1983

Related U.S. Application Data

[63] Continuation of Ser. No. 349,539, Feb. 17, 1982, abandoned.

[30] Foreign Application Priority Data

Feb. 18, 1981 [FR] France .................................. 81 03199
Dec. 10, 1981 [FR] France .................................. 81 23098

[51] Int. Cl.⁴ ........................ A61K 7/04; A61K 31/74
[52] U.S. Cl. ......................................... 424/61; 424/78
[58] Field of Search .................. 424/61, 78; 526/307.7

[56] References Cited

U.S. PATENT DOCUMENTS

| | | | |
|---|---|---|---|
| 2,311,548 | 2/1943 | Jacobsen et al. | 526/307.7 |
| 3,478,756 | 11/1969 | Sautter et al. | 424/61 |
| 3,547,950 | 12/1970 | Gander | 524/462 |
| 3,749,769 | 7/1973 | Sugiyama et al. | 424/61 |
| 3,804,784 | 4/1974 | Esbitt | 524/32 |
| 3,989,777 | 11/1976 | Strawson et al. | 264/24 |
| 4,057,624 | 11/1977 | Hase et al. | 424/78 |
| 4,126,675 | 11/1978 | Boulogne et al. | 424/61 |
| 4,158,053 | 6/1979 | Greene et al. | 424/61 |
| 4,425,326 | 1/1984 | Guillon et al. | 424/61 |

FOREIGN PATENT DOCUMENTS 1074201 6/1967 United Kingdom ................. 424/61
2073229 10/1981 United Kingdom .

Primary Examiner—Sidney Marantz
Assistant Examiner—Shawn P. Foley
Attorney, Agent, or Firm—Parkhurst & Oliff

[57] ABSTRACT

Nail lacquer compositions comprising a polymer resin consisting essentially of units resulting from the copolymerization of:

(1) 75 to 97% by weight of at least one monomer having the general formula:

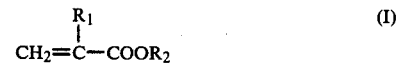

in which:

$R_1$ represents an hydrogen atom or a methyl radical, and $R_2$ represents a linear alkyl radical or a branched radical having 1 to 18 carbon atoms, a mono or dihydroxy alkyl radical, the alkyl radical having from 2 to 4 carbon atoms, a glycidyl radical or the radical $-(CH_2)_n-OR'$, wherein $R'$ represents methyl or ethyl and n is 3 or 4, and (2) 3 to 25% by weight of at least one monomer selected from the group consisting of N-vinylsulfonamide, 4-styrenesulfonamide, acrylamide, methacrylamide, N-(N'N',3-dimethylaminopropyl) methacrylamide and N-(N'N',3-dimethylaminopropyl) acrylamide.

9 Claims, No Drawings

ANHYDROUS NAIL LACQUER CONTAINING AS A RESIN A COPOLYMER COMPRISING UNITS OF VINYLSULFONAMIDE OR A UNSATURATED AMIDE AND OF AN ALKYL ACRYLATE OR METHACRYLATE

This application is a continuation of Ser. No. 349,539, filed Feb. 17, 1982, now abandoned.

The present invention concerns the field of manicure products and notably colored or colorless nail varnish or lacquer.

Nail lacquers must exhibit, as principal characteristics, no irritation of the skin or nails, easy application, storage stability, good brilliance and excellent adhesion on the keratin of the nails.

Furthermore, it is important that the flexibility of the film left on the surface of the nail be satisfactory to ensure that the lacquer does not break or crack.

The compositions of nail lacquers are essentially based on the use of a mixture of polymers comprising nitrocellulose and an aryl sulfonamide formaldehyde resin of low molecular weight known under the name SANTOLITE.

This resin plays the role of plasticizing the nitro-cellulose thus to permit assurance of good adhesion and good flexibility of the lacquer on the nail.

The actual trend is to replace the nitrocellulose and the SANTOLITE with certain copolymers, and notably with copolymers having a base of acrylate or methacrylate with a view to correcting certain of the inconveniences which accompany use of these substances. These inconveniences, in that they concern the nitrocellulose, are essentially the risks entrained by its manipulation, and evolution of its chemical structure as a function of time.

Inasmuch as it concerns the SANTOLITE the principal inconvenience is the liberation of formaldehyde as a function of time.

Nevertheless, it is established that use of these copolymers with an acrylate or methyacrylate base does not enable conferring an excellent adhesion to the keratin of the nail.

By employing a certain class of copolymers comprising notably units of vinylsulfonamide, of acrylamide or methacrylamide, or of an unsaturated amino alkyl amide, it has been established that it was possible to overcome these inconveniences.

The present invention has an object by way of a new industrial product an anhydrous nail lacquer comprising a resin, and a solvent system wherein said resin comprises a copolymer consisting essentially of units resulting from the copolymerization of:

(1) 75 to 97% by weight of at least one monomer having the general formula:

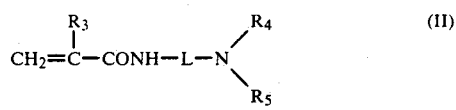

in which:

$R_1$ represents a hydrogen atom or a methyl radical, and $R_2$ represents a linear alkyl radical or branched alkyl radical having 1 to 18 carbon atoms, a mono- or dihydroxyalkyl radical, the alkyl radical having from 2 to 4 carbon atoms, a glycidyl radical or the radical —$(CH_2)_n$—OR′, wherein R′ represents methyl or ethyl and n is 3 or 4, and (2) 3 to 25% by weight of at least one monomer selected from the group consisting of: N-vinylsulfonamide, 4-styrene sulfonamide, acrylamide, methacrylamide and an unsaturated aminoalkyl amide of the general formula:

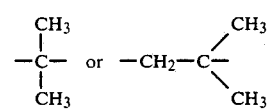

in which: $R_3$ represents a hydrogen atom or a methyl radical, L represents an alkylene radical 2 to 6 carbon atoms or a substituted alkylene radical having from 2 to 4 carbon atoms and notably the radicals of the formula:

and $R_4$ and $R_5$ are either identical or different and represent a hydrogen atom, a methyl or ethyl radical, said units of formula (II) being optionally present in quaternized or salified form.

These copolymers are essentially bipolymers, but may also be terpolymers, tetrapolymers, or higher polymers in so far as more than one monomer of each of the two groups mentioned above is used.

Among the monomers of formula (I), there can be cited in particular the acrylates and methacrylates of methyl, ethyl, propyl, butyl, hexyl, dodecyl, hexadecyl, octadecyl, glycidyl, 2,3-dihydroxypropyl, 2-hydroxyethyl, 3-hydroxypropyl and ω-methyl or ethyl polyethylene glycol.

Among the monomers of formula (II) there can be cited in particular N-(N′,N′,3-dimethylamino propyl)-methacrylamide, N-(N′,N′,3-dimethylamino propyl)acrylamide and the like.

The quaternization agents are preferably ethylbromide and dimethylsulfate, and the salifying agents, acetic acid and lactic acid.

The proportion of vinylsulfonamide, 4-styrene sulfonamide, acrylamide, methacrylamide or the monomer of formula (II) is established to be critical with a view to obtaining good properties of the film and notably good adhesion to the keratin of the nail.

The polymers according to the invention have a molecular weight generally between 600 and 100,000 and preferably between 1000 and 40,000 measured by osmometry.

The copolymers used in the compositions of lacquer according to the invention are able to be obtained by diverse processes of conventional polymerization such as, for example, suspension, mass, emulsion or solution polymerization. Preferably, the polymerization is carried out in solution in an organic solvent such as ethyl acetate, butyl acetate, acetone, or the like.

According to this solution polymerization process it possible to use as catalysts the peroxides, peresters, percarbonates, and notably benzoyl peroxide, di-tert-butyl peroxide, 2-tert-butyl-peroxyethyl hexanoate, 4-bis-tert-butylcyclohexyl peroxydicarbonate or azo-bis-isobutyronitrile.

As polymerization initiators it is also possible to use oxydo reduction systems or to subject the reaction mixture to UV radiation with a view to provoking the formation of free radicals.

The time of reaction is generally between 2 and 24 hours at a temperature between about 25° and 80° C.

After the completion of the polymerization reaction, the copolymer is obtained by precipitation with the aid of a solvent in which the polymer is not soluble such as, for example, petroleum ether or additionally certain mixtures of solvents.

The amount of polymerization initiator may be between about 0.3 and 15% with respect to the total weight of the monomers to be reacted.

When the copolymers comprise units of formula (II) quaternized or salified, the quaternization or salification is preferably carried out after the copolymerization.

Various examples of preparation of copolymers useful as the nail lacquer of the present invention are described hereafter. The nail lacquers according to the invention, which may be colored or colorless, preferably contain 3 to 35% by weight of a copolymer such as that defined above, with the remainder consisting essentially of the solvent mixture of the nail lacquer, i.e. the usual solvents and or conventional diluents for such types of compositions.

However, in preferential fashion, the lacquers contain in addition 0.2 to 10% by weight of at least one plasticizer with a view to improving the adherence and flexibility of the film.

As plasticizers there can be cited tricresyl phosphate, benzyl benzoate, tributyl phosphate, butyl acetyl ricinoleate, glyceryl acetyl ricinoleate, dibutyl phthalate, butyl glycolate, dioctyl phthalate, butyl stearate, tributoxy ethyl phosphate, triphenyl phosphate, triethyl citrate, tributyl citrate, tributyl acetyl citrate, 2-triethylhexyl acetyl citrate, dibutyl tartrate, dimethoxy ethyl phthalate, di-isobutyl phthalate, diamyl phthalate, camphor, glycerol triacetate and mixtures thereof.

Although with the nail lacquers according to the invention it is possible to avoid the use of nitrocellulose and/or the resin of the aryl sulfonamide formaldehyde type, it is nevertheless useful to introduce in the lacquers a certain amount although clearly less than that which is generally required.

The nitrocelluloses are of the type "RS" or "SS" and in particular the nitrocellulose type ¼ second RS, nitrocellulose type ½ second RS and nitrocellulose type RS ¾ second.

Preferably one utilizes according to the invention the type RS nitrocellulose.

The resins of the arylsulfonamide formaldehyde type are those known under the commercial names of "SANTOLITE MHP" and "SANTOLITE MS 80%", the former being harder while the latter produces films of greater flexibility.

The solvent system or mixture of the lacquer according to the invention is obtained from volatile organic solvents or mixtures thereof.

It is thus possible to obtain a relatively short drying time. Among the solvents there can be cited acetone, ethylacetate, butylacetate, 2-methoxyethylacetate, methylethylketone, methylisobutylketone and methylacetate.

Further the solvent system or mixture comprises also a diluent and preferably an aromatic organic solvent such as toluene or xylene in a proportion generally comprised between 10 and 30% with respect to the total weight of the lacquer.

The lacquers can also contain other volatile solvents such as ethanol, n-butanol, n-propanol, isopropanol or mixtures thereof, these volatile solvents are preferably employed when the polishes contain a certain amount of nitrocellulose.

The nail lacquers, when they are colored, contain at least one known coloring agent of organic or inorganic nature. Preferred organic coloring agents include: D and C Red Nos. 10, 11, 12 and 13, D and C Red No. 7, D and C Red Nos. 5 and 6, D and C Red No. 34, the lakes such as the lake D and C Yellow No. 5, and the lake D and C Red No. 2. Preferred inorganic coloring agents include: titanium dioxide, bismuth oxychloride, brown iron oxide, red iron oxides, and guanine.

These coloring agents are preferably present in the lacquer in a proportion comprising between 0.1 and 8% by weight with respect to the total weight of the composition.

The lacquer according to the invention can also contain other ingredients such as, for example, any of a number of known products which permit avoiding sedimentation. Notable among these are the silicon derivatives or the clays of the montmorillonite type such as "Bentone 27" or "Bentone 38" and the like in the presence of a swelling agent such as orthophosphoric acid.

The lacquers once applied on the nails can easily and only be removed by using the conventional removers which consist of simple mixtures of organic solvents such as acetone, amyl acetate or ethyl acetate and which may contain small amounts of fatty material to counteract any excessive drying action of the solvents on the nails.

The following Examples further illustrate the present invention and the preparation of the copolymers used in the nail lacquer compositions according to the invention.

EXAMPLE 1

Copolymer of 60% methylacrylate/35% hexylmethacrylate/5% N-(N',N',3-dimethylaminopropyl)methacrylamide In a 500 cc flask having a mechanical agitator and refrigerant and a tube for introducing nitrogen, one introduces 60 grams of methacrylate, 35 grams of hexylmethacrylate and 5 grams of N-(N',N'3-dimethylaminopropyl)methacrylamide, 2 grams of azo-bis-isobutyronitrile crystalized in ethanol and 100 grams of ethylacetate.

The reaction mixture is heated under agitation with reflux for 15 hours. After cooling the solution is diluted with 100 grams of ethylacetate after which the polymer is precipitated by addition of 6.5 liters of petroleum ether. After drying one obtains the polymer with a yield of 75%.

Viscosity: 0.88 cPo (5% solution in ethylacetate at 34.6° C.)

EXAMPLE 2

Copolymer of 65% butylmethacrylate/30% ethylacrylate/5% N-(N',N',3-dimethylaminopropyl)acrylamide This copolymer has been prepared according to the same method as described in Example 1 and one obtains the expected polymer with a yield of 78%. Viscosity: 0.90 cPo (5% solution in ethylacetate at 34.6° C.)

According to the same method as described in Example 1, one also prepares the following copolymer: 8%

N-(N',N',3-dimethylaminopropyl)methacrylamide/60% butylmethacrylate/22% ethylacrylate/10% laurylmethacrylate.

Viscosity: 0.95 cPo (5% solution in ethylacetate at 34.6° C.)

EXAMPLE 3

Copolymer of 10% 4-styrene sulfonamide/61% butylmethacrylate/29% ethylacrylate

In a flask having an agitator and an inflow of nitrogen one introduces 2.5 grams of 4-styrene sulfonamide, 15.22 grams of butylmethacrylate, 7.28 grams of ethylacrylate, 0.25 grams of azo-bis-isobutyronitrile and 50 grams of dimethylformamide.

The reaction mixture is heated at 50° C. for 23 hours under agitation and under a nitrogen atmosphere and then is poured into water. The precipitated polymer is then dissolved in tetrahydrofuran and reprecipitated with water. After drying, the polymer is dissolved in 40 grams of ethylacetate, the unreacted 4-styrene sulfonamide remaining in suspension in the ethylacetate. The 4-styrene sulfonamide is eliminated by centrifuging the solution for 1 hour.

After evaporation of the solvent 8 grams of the expected polymer are obtained.

Viscosity: 1.05 cPo (5% solution in ethylacetate at 34.6° C.)

According to the same method of preparation, as described in Example 3, the following copolymers were also obtained:

3% 4-styrene sulfonamide/5% N-(N',N',3-dimethylaminopropyl)acrylamide/60% butylmethacrylate/22% ethylacrylate.

Viscosity: 1.05 cPo (5% solution in ethylacetate at 34.6° C.)

20% 4-styrene sulfonamide/53% butylmethacrylate/27% ethylacrylate.

Viscosity: 0.98 cPo (5% solution in ethylacetate at 34.6° C.)

EXAMPLE 4

Copolymer of 6% methacrylamide/47% ethylacrylate/47% butylmethacrylate

In a 500 cc flask having a mechanical agitator, a refrigerant and a tube for introducing nitrogen, one places 47 grams of ethylacrylate, 47 grams of butylmethacrylate, 6 grams of methacrylamide, 1 gram of azo-bis-isobutyronitrile and 200 grams of ethylacetate.

The reaction mixture is heated under agitation with reflux for 16 hours. After cooling, the solution is precipitated in 7 liters of petroleum ether. After drying, one obtains the polymer with a yield of 85%.

Viscosity: 1.18 cPo (5% solution in ethyl acetate at 34.6° C.)

EXAMPLE 5

Copolymer of 10% acrylamide/45% ethylacrylate/45% butyl methacrylate

This copolymer is obtained according to the same method as described in Example 4 with a yield of 78%.

Viscosity: 0.05 cPo (5% solution in ethyl acetate at 34.6° C.)

EXAMPLE 6

Copolymer of 8% methacrylamide/46% methyl methacrylate/46% hexylmethacrylate

This copolymer is obtained according to the same method as described in Example 4 with a yield of 80%.

Viscosity: 1.10 cPo (5% solution in ethyl acetate at 34.6° C.)

EXAMPLE 7

Copolymer of 4% 4-styrene sulfonamide/96% butylmethacrylate

This bipolymer is obtained according to the same method as described in example 4 with a yield of 68%.

Viscosity: 1.25 cPo (5% solution in ethyl acetate at 34.6° C.)

EXAMPLE 8

Copolymer of 10% methacrylamide/90% butylmethacrylate

This bipolymer is obtained according to the same method as described in example 4 with a yield of 73%.

Viscosity: 1.06 cPo (5% solution in ethyl acetate.)

EXAMPLE 9

Copolymer of 20% methacrylamide/80% hexylmethacrylate

This bipolymer is obtained according to the same method as described in example 4 with a yield of 82%.

Viscosity: 0.97 cPo (5% solution in ethylacetate at 34.6° C.)

EXAMPLE 10

Copolymer of 15% methacrylamide/85% ethylacrylate

This bipolymer is obtained according to the same method as described in example 4 with a yield of 75%.

Viscosity: 1.02 cPo (5% solution in ethyl acetate at 34.6° C.)

EXAMPLE 11

Copolymer of 5% N-(N',N',3-dimethylamino propyl)acrylamide/95% butyl methacrylate This bipolymer is obtained according to the same method as described in example 4 with a yield of 71%.

Viscosity: 1.10 cPo (5% solution in ethyl acetate at 34.6° C.)

EXAMPLE 12

Copolymer of 70% butyl methacrylate/10% ethyl acrylate/10% hydroxy-2 propyl methacrylate/10% methacrylamide In a 500 cc flask having a mechanical agitator, a refrigerant and a tube for introducing nitrogen, are introduces 70 grams of butyl methacrylate, 10 grams of ethyl acrylate, 10 grams of hydroxy-2 propyl methacrylate, 10 grams of methacrylamide, 150 grams of ethyl acetate and 0,2 grams of azo-bis-isobutyronitrile.

The reaction mixture is heated under agitation with reflux for 15 hours. After cooling the solution is diluted with 150 grams of ethyl acetate and then poured on 7 liters of petroleum ether.

After drying are obtains the polymer with a yield of 70%.

Viscosity: 0.56 cPo (1% solution in ethyl acetate at 25° C.)

Examples of Nail Lacquers

EXAMPLE A

A colorless nail lacquer is prepared according to the invention by mixing the following ingredients:

| | |
|---|---|
| Copolymer of Example 1 | 25 gr. |
| Butyl phtalate | 4 gr. |
| Camphor | 1 gr. |
| Ethyl acetate | 20 gr. |
| Butyl acetate | 28 gr. |
| Toluene | 22 gr. |

The lacquer is applied on the nails with the aid of a brush permitting formation of a uniform film which presents after drying good adhesion and good brilliance.

EXAMPLE B

A colored nail lacquer is prepared according to the invention by mixing the following ingredients:

| | |
|---|---|
| Copolymer of Example 2 | 24 gr. |
| Butyl phtalate | 7 gr. |
| Ethyl acetate | 16 gr. |
| Toluene | 18.5 gr. |
| Camphor | 2 gr. |
| Titanium oxide | 1 gr. |
| D and C RED 7 - Lake of calcium | 0.5 gr. |
| D and C RED 34 | 0.3 gr. |
| D and C YELLOW 5 - Lake of aluminum | 0.7 gr. |
| Butyl acetate | 30 gr. |

In this Example the copolymer, according to Example 2, can advantageously be replaced by the copolymer 8% N-(N',N', 3-dimethylamino propyl) acrylamide/60% butylmethacrylate/10% laurylmethacrylate/22% ethylacrylate.

EXAMPLE C

A colorless nail lacquer is prepared according to the invention by mixing the following ingredients:

| | |
|---|---|
| Copolymer of Example 2 | 5 gr. |
| Ethyl acetate | 30 gr. |
| Butyl acetate | 40 gr. |
| Butyl phtalate | 3 gr. |
| Camphor | 2 gr. |

In this Example, the copolymer can be replaced by the same amount of copolymer according to Example 3.

EXAMPLE D

A colorless nail lacquer is prepared according to the invention by mixing the following ingredients:

| | |
|---|---|
| Copolymer of 20% 4-styrene sulfonamide/53% butylmethacrylate/27% ethyl acrylate | 25 gr. |
| Butyl phtalate | 4 gr. |
| Camphor | 1 gr. |
| Ethyl acetate | 20 gr. |
| Butyl acetate | 28 gr. |
| Toluene | 22 gr. |

In this example, the copolymer used can be replaced by the same amount of the copolymer: 3% 4-styrene sulfonamide/5% N-(N',N',3-dimethylamino propyl) acrylamide/60% butyl methacrylate/22% ethylacrylate.

EXAMPLE E

A colored lacquer is prepared according to the invention by mixing the following ingredients:

| | |
|---|---|
| Copolymer of Example 4 | 24 gr. |
| Butyl phtalate | 7 gr. |
| Ethyl acetate | 16 gr. |
| Toluene | 18.5 gr. |
| Camphor | 2 gr. |
| Titanium oxide | 1 gr. |
| D and C RED 7 - Lake of calcium | 0.5 gr. |
| D and C RED 34 | 0.3 gr. |
| D and C YELLOW 5 - Lake of aluminum | 0.7 gr. |
| Butyl acetate | 30 gr. |

EXAMPLE F

A colorless nail lacquer is prepared according to the invention by mixing the following ingredients:

| | |
|---|---|
| Copolymer of Example 6 | 25 gr. |
| Butyl acetate | 40 gr. |
| Ethyl acetate | 30 gr. |
| Butyl phtalate | 3 gr. |
| Camphor | 2 gr. |

EXAMPLE G

A colorless nail lacquer is prepared according to the invention by mixing the following ingredients:

| | |
|---|---|
| Copolymer of Example 5 | 25 gr. |
| Butyl phtalate | 4 gr. |
| Camphor | 1 gr. |
| Ethyl acetate | 20 gr. |
| Butyl acetate | 28 gr. |
| Toluene | 22 gr. |

When the nail lacquers of Examples E through G are applied to the nails with the aid of a brush, one obtains a uniform film which present after drying excellent adhesion and good brilliance.

In this example the copolymer of example 5 can be replaced by the same amount of the bipolymer of example 10.

EXAMPLE H

A colored nail lacquer is prepared by mixing the following ingredients:

| | |
|---|---|
| Copolymer of Example 9 | 24 gr. |
| Butyl phtalate | 7 gr. |
| Ethyl acetate | 16 gr. |
| Toluene | 18.5 gr. |
| Camphor | 2 gr. |
| Titanium oxide | 1 gr. |
| D and C RED 7 - Lake of calcium | 0.5 gr. |
| D and C RED 34 | 0.3 gr. |
| D and C YELLOW 5 - Lake of Aluminium | 0.7 gr. |
| Butyl acetate | 30 gr. |

In this example, the bipolymer of Example 9 can be replaced by the same amount of the copolymers of examples 8 and 10.

EXAMPLE I

A coloured nail lacquer is prepared according to the invention by mixing the following ingredients:

| | |
|---|---|
| Copolymer of Example 7 | 5 gr. |
| Santolite MHP | 5 gr. |
| ⅛ record nitrocellulose | 12 gr. |
| Isopropyl alcohol | 3 gr. |
| Butyl alcohol | 3 gr. |
| Camphor | 1 gr. |
| Tricresyl phosphate | 3 gr. |
| 2-methoxy ethyl acetate | 5 gr. |
| Ethyl acetate | 12 gr. |
| Toluene | 18 gr. |
| Bentone 27 | 2 gr. |
| Titanium oxide | 0.5 gr. |
| Prussian Blue | 0.2 gr. |
| D and C YELLOW 5 - aluminium Lake | 0.5 gr. |
| D and C RED 9 | 0.3 gr. |
| D and C RED 11 | 0.4 gr. |
| Butyl acetate q.s.p. | 100 gr. |

In this example the bipolymer of Example 7 can be replaced by the same amount of the copolymer of example 11.

EXAMPLE J

A colorless nail lacquer is prepared according to the invention by mixing the following ingredients:

| | |
|---|---|
| Copolymer of example 12 | 25 gr. |
| Butyl phtalate | 4 gr. |
| Camphor | 1 gr. |
| Ethyl acetate | 20 gr. |
| Butyl acetate | 28 gr. |
| Toluene | 22 gr. |

EXAMPLE K

A colored nail lacquer is prepared according to the invention by mixing the following ingredients:

| | |
|---|---|
| Copolymer of example 12 | 24 gr. |
| Butyl phtalate | 7 gr. |
| Ethyl acetate | 16 gr. |
| Toluene | 18 gr. |
| Camphor | 2 gr. |
| Titanium oxide | 1 gr. |
| D and C RED 7 - lake of calcium | 0.5 gr. |
| D and C RED 34 | 0.3 gr. |
| D and C YELLOW 5 - Lake of aluminium | 0.7 gr. |
| Butyl acetate | 30 gr. |

What is claimed is:

1. A nail lacquer comprising a resin and a solvent system, said nail lacquer being anhydrous and said polymer resulting from the copolymerization of:

(1) 75 to 97% by weight of at least one monomer selected from the group consisting of acrylate of ω-methyl or ethyl polyethylene glycol, methacrylate of ω-methyl or ethyl polyethylene glycol and a monomer of the formula:

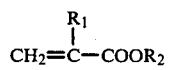

$$CH_2=\overset{R_1}{\underset{|}{C}}-COOR_2$$

in which:

$R_1$ represents a hydrogen atom or a methyl radical and $R_2$ represents a linear alkyl radical or branched alkyl radical having 1 to 18 carbon atoms, a mono or dihydroxy alkyl radical, the alkyl radical having from 2 to 4 carbon atoms and a glycidyl radical, and (2) 3 to 25% by weight of at least one monomer selected from the group consisting of N-vinylsulfonamide, 4-styrenesulfonamide, acrylamide and methacrylamide, said copolymer being present in an amount of 3 to 35% by weight of the nail lacquer composition.

2. The lacquer of claim 1, wherein said copolymer results from the copolymerization of:

(1) 75 to 97% by weight of at least one monomer selected from the group consistng of methyl acrylate, ethyl acrylate, propyl acrylate, butyl acrylate, hexyl acrylate, dodecyl acrylate, hexadecyl acrylate, octadecyl acrylate, glycidyl acrylate, 2,3-dihydroxypropyl acrylate, 2-hydroxyethyl acrylate, 3-hydroxypropyl acrylate, acrylate of ω-methyl or ethyl polyethylene glycol and the methacrylates thereof and (2) 3 to 25% by weight of at least one monomer selected from the group consisting of N-vinylsulfonamide, 4-styrenesulfonamide, acrylamide and methacrylamide.

3. Lacquer according to claim 1, which additionally comprises an agent for avoiding sedimentation and a swelling agent.

4. Lacquer according to claim 3 wherein said antisedimentation agent is a clay of the montmorillonite type, and said swelling agent is phosphoric acid.

5. The lacquer of claim 1, wherein said copolymer has a molecular weight between 600 and 100,000 measured by osmometry.

6. The lacquer of claim 1, which also contains from 0.2 to 10% by weight of a plasticizer.

7. The lacquer of claim 1, which also contains an organic or inorganic coloring agent in an amount from 0.1 to 8% by weight of the total lacquer.

8. A nail lacquer comprising a resin and a solvent system, said nail lacquer being anhydrous and said resin comprising a copolymer resulting from the copolymerization of:

(1) 75 to 97% by weight of at least one monomer selected from the group consisting of methyl acrylate, ethyl acrylate, propyl acrylate, butyl acrylate, hexyl acrylate, dodecyl acrylate, hexadecyl acrylate, octadecyl acrylate, glycidyl acrylate, 2,3-dihydroxypropyl acrylate, 2-hydroxyethyl acrylate, 3-hydroxypropyl acrylate, acrylate of ω-methyl or ethyl polyethylene glycol and the methacrylates thereof, and (2) 3 to 25% by weight of at least one monomer selected from the group consisting of N-vinylsulfonamide, 4-styrenesulfonamide, acrylamide, methacrylamide, N-(N',N'-3-dimethylaminopropyl)methacrylamide and N-(N',N'-3-dimethylaminopropyl)acrylamide, said copolymer containing units selected from the group consisting of N-(N',N'-3-dimethylaminopropyl)methacrylamide and N-(N',N'-3-dimethylaminopropyl)acrylamide, said copolymer being quaternized with a quaternizing agent selected from the group consisting of ethylbromide and dimethylsulfate, and said copolymer being present in an amount of 3 to 35% by weight of the nail lacquer composition.

9. A nail lacquer comprising a resin and a solvent system, said nail lacquer being anhydrous and said resin comprising a copolymer resulting from the copolymerization of:
(1) 75 to 97% by weight of at least one monomer selected from the group consisting of methyl acrylate, ethyl acrylate, propyl acrylate, butyl acrylate, hexyl acrylate, dodecyl acrylate, hexadecyl acrylate, octadecyl acrylate, glycidyl acrylate, 2,3-dihydroxypropyl acrylate, 2-hydroxyethyl acrylate, 3-hydroxypropyl acrylate, acrylate of ω-methyl or ethyl polyethylene glycol and the methacrylates thereof, and
(2) 3 to 25% by weight of at least one monomer selected from the group consisting of N-vinylsulfonamide, 4-styrenesulfonamide, acrylamide, methacrylamide, N-(N',N'-3-dimethylaminopropyl)methacrylamide and N-(N',N'-3-dimethylaminopropyl)acrylamide, said copolymer containing units selected from the group consisting of N-(N',N'-3-dimethylaminopropyl)methacrylamide and N-(N',N',-3"dimethylaminopropyl)acrylamide, said copolymer being salified with a salifying agent selected from the group consisting of acetic acid and lactic acid, and said copolymer being present in an amount of 3 to 35% by weight of the nail lacquer composition.

* * * * *